United States Patent [19]

Seitz et al.

[11] Patent Number: 5,932,567

[45] Date of Patent: Aug. 3, 1999

[54] THROMBIN INHIBITORS

[75] Inventors: Werner Seitz, Plankstadt; Helmut Mack, Ludwigshafen; Thomas Zierke, Iggelheim; Hans-Joachim Böhm, Limburgerhof; Hans Wolfgang Höffken; Stefan Koser, both of Ludwigshafen; Thomas Pfeiffer, Böhl-Iggelheim; Wilfried Hornberger, Neustadt, all of Germany

[73] Assignee: BASF Aktiengesellschaft, Ludwigshafen, Germany

[21] Appl. No.: 08/875,515

[22] PCT Filed: Feb. 6, 1996

[86] PCT No.: PCT/EP96/00472

§ 371 Date: Jul. 30, 1997

§ 102(e) Date: Jul. 30, 1997

[87] PCT Pub. No.: WO96/24609

PCT Pub. Date: Aug. 15, 1996

[30] Foreign Application Priority Data

Feb. 10, 1995 [DE] Germany .............................. 195/04/504
Feb. 24, 1995 [DE] Germany .............................. 195/06/610

[51] Int. Cl.$^6$ ........................ C07D 239/14; A61K 38/55
[52] U.S. Cl. ........................ 514/210; 514/317; 514/343; 514/354; 514/423; 540/1; 546/192; 546/278.4; 546/332; 548/537

[58] Field of Search ................................. 546/192, 278.4, 546/332; 514/317, 210, 343, 354, 432; 540/1; 548/537

[56] References Cited

FOREIGN PATENT DOCUMENTS

| 601 459 | 6/1994 | European Pat. Off. . |
| 669 317 | 8/1995 | European Pat. Off. . |
| 672 658 | 9/1995 | European Pat. Off. . |
| 94/29336 | 12/1994 | WIPO . |
| 95/23609 | 9/1995 | WIPO . |

Primary Examiner—Zinna Northington Davis
Attorney, Agent, or Firm—Keil & Weinkauf

[57] ABSTRACT

Thrombin inhibitors of the formula

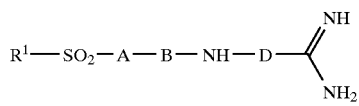

where $R^1$, A, B and D have the meaning indicated in the description, and intermediates for the preparation thereof are described.

The compounds I are suitable for controlling diseases.

5 Claims, No Drawings

THROMBIN INHIBITORS

This application is a 371 of PCT/EP96/00472 filed Feb. 6, 1996.

The present invention relates to p-amidinobenzylamides of peptides with N-terminal sulfonyl or aminosulfonyl radicals, to the preparation thereof and to the use thereof as thrombin inhibitors.

EP 601 459, EP 672 658, WO 94/29336 and WO 95/23609 describe peptide thrombin inhibitors.

The present invention relates to thrombin inhibitors of the formula I

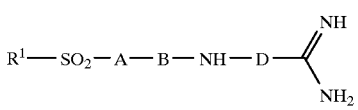

and the stereoisomers thereof and the salts thereof with physiologically tolerated acids, where the amidine functionality can be in mono- or diprotected form and in which the substituents have the following meanings:

$R^1$ OH, $C_1$–$C_{20}$-alkyl, $C_1$–$C_3$-fluoroalkyl, $C_3$–$C_8$-cycloalkyl, aryl-$C_1$–$C_{10}$-alkyl, aryl, hetaryl, $R^2$OOC—$(CH_2)_n$ or $R^3R^2N$, where $R^2$ and $R^3$ are identical or different and are hydrogen, $C_1$–$C_{10}$-alkyl, aryl, aryl-$C_1$–$C_{10}$-alkyl or together are a $C_2$–$C_7$-alkylene chain to which an aryl or hetaryl radical can be fused or which can contain a hetero atom (O, S, NH or substituted N), and n is 1, 2, 3 or 4, A: an α-amino acid residue of the formula II

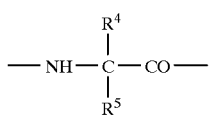

where $R^4$ is hydrogen, $C_1$–$C_8$-alkyl, $C_3$–$C_7$-cycloalkyl, aryl or aryl-$C_1$–$C_3$-alkyl, $R^5$ is hydrogen, $C_1$–$C_8$-alkyl, $C_3$–$C_7$-cycloalkyl or $C_3$–$C_7$-cycloalkyl-$CH_2$—, it being possible for a $CH_2$ group in the ring to be replaced by O, S, $NR^6$, or bicycloalkyl-$(CH_2)_{0,1}$ [sic], adamantyl-$(CH_2)_{0-1}$, $(CH_3)_3Si$—$C_1$–$C_4$-alkyl, aryl or aryl-$C_1$–$C_3$-alkyl, hetaryl or hetaryl-$C_1$–$C_3$-alkyl, if $R^4$ is H, a $C_1$–$C_8$-alkyl radical in which a hydrogen atom is replaced by $SR^6$, $OR^6$, CO—$OR^6$ ($R^6$=hydrogen, $C_1$–$C_8$-alkyl or aryl-$C_1$–$C_3$-alkyl) or $CONR^7R^8$ ($R^7$, $R^8$ are identical or different and are H, $C_1$–$C_4$-alkyl, $C_3$–$C_7$-cycloalkyl or together are a $C_3$–$C_6$-alkylene chain), or $R^4$ and $R^5$ together are a $C_2$–$C_6$-alkylene chain which may contain a fused-on aryl radical, B: a cyclic α-amino acid residue of the formula III

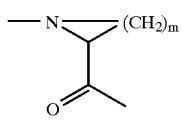

where m is 2, 3 or 4, and a hydrogen on the ring can be replaced by a hydroxyl or $C_1$–$C_3$-alkyl group and, if m is 3 or 4, a $CH_2$ group in the ring can be replaced by oxygen, sulfur, NH or N—$C_1$–$C_4$-alkyl and/or two vicinal hydrogen atoms can be replaced by a double bond or by a fused-on aromatic system or a methylene chain with 4–6 carbon atoms, D: a structural fragment of the formula IV, V or VI

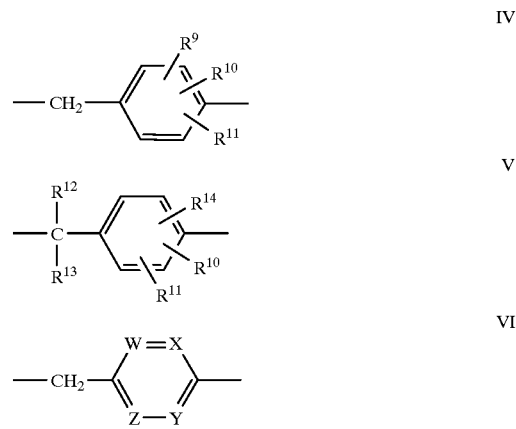

where $R^9$ is F, Cl, Br, $NO_2$, $R^{15}O$, $R^{15}OOC$, $R^{15}OCH_2$, $R^{15}NH$, $R^{15}CONH$, $R^{15}NH$—CO or $R^{15}OOCCH_2O$, where $R^{15}$ is H, $C_1$–$C_6$-alkyl, benzyl or phenyl, $R^{10}$, $R^{11}$ are H, $C_1$–$C_4$-alkyl or $R^{15}O$, where $R^9$ and $R^{10}$ or $R^{11}$ may together form a fused-on phenylene ring or an alkylene chain consisting of 3 to 5 carbon atoms, in which one or two carbon atoms can be replaced by oxygen, $R^{12}$ is H or $C_1$–$C_4$-alkyl, $R^{13}$ is $C_1$–$C_4$-alkyl, phenyl-$C_1$–$C_4$-alkyl, $R^{15}CO$, $CF_3CO$, $C_2F_5CO$, $R^{15}OCH_2$, $R^{15}OOC$, $R^{15}OCH_2CO$, $R^{15}OOCCO$ or $R^{15}NHCOCO$, $R^{14}$ is H, $C_1$–$C_4$-alkyl, F, Cl, Br, $NO_2$, $R^{15}O$, $R^{15}OOC$, $R^{15}OCH_2$, $R^{15}NH$, $R^{15}CONH$, $R^{15}NH$—CO or $R^{15}OOCCH_2O$, and W, X, Y, Z are CH or N, but at least one of the radicals W, X, Y or Z is N and the ring in VI can be substituted by 1 or 2 of the following radicals: $C_1$–$C_4$-alkyl, OH, O—$C_1$–$C_4$-alkyl, $CF_3$, F, Cl, Br, S—$C_1$–$C_4$-alkyl, $O(CH_2)_n$ $COOR^6$ (n=1–4).

The term "aryl" everywhere means mono- or bicyclic aromatic groups which contain 6 to 10 carbon atoms in the ring system, eg. phenyl or naphthyl, and which can be provided with up to three identical or different substituents.

The term "hetaryl" everywhere refers to 5- or 6-membered aromatic rings which may contain 1 or 2 hetero atoms such as N, O or S and to which an aryl ring, for example a phenyl ring, can be fused.

The term "cycloalkyl" means saturated cyclic hydrocarbon radicals with 3 to 7 carbon atoms, eg. cyclopentyl, cyclohexyl, cycloheptyl, it being possible for the rings to be substituted by halogen, $C_1$–$C_4$-alkyl and O—$C_1$–$C_4$-alkyl.

The following compound groups Ia to Ig are preferred:

Ia:

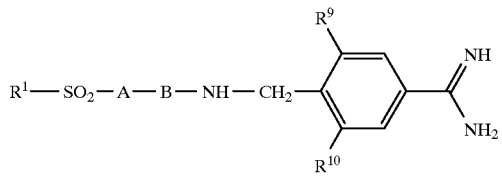

and

Ib:

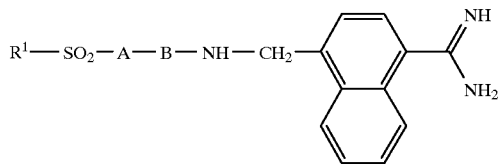

Herein, the substituents R and the fragments A and B have the following meanings:

$R^1$: OH, $C_1$–$C_{10}$-alkyl, $CF_3CH_2$, phenyl, naphthyl, phenyl-$C_1$–$C_4$-alkyl (especially benzyl and phenethyl), naphthyl-$C_1$–$C_4$-alkyl, pyridyl, isoquinolyl, $NH_2$, $C_1$–$C_4$-mono- and dialkylamino, piperidinyl.

A: glycine, alanine, valine, leucine, isoleucine, phenyl- and cyclohexylglycine, phenyl- and cyclohexylalanine, tetrahydropyranylglycine, tetrahydropyranylvaline, α-methylcyclohexylalanine, diphenyl- and dicyclohexylalanine, it being possible for phenyl rings present in the residues to be substituted by up to three identical or different $C_1$–$C_4$-alkyl, O—$C_1$–$C_4$-alkyl, OH, F, Cl or $COOR^6$ radicals, aspartic acid, glutamic acid, asparagine, glutamine, the nitrogen atom possibly carrying, if required, one or two alkyl groups or being part of a $C_4$–$C_8$-ring, serine, homoserine, threonine, it being possible for the carboxyl or hydroxyl group to be esterified or etherified by a $C_1$–$C_8$-alkyl radical.

The amino acids A preferably have the D configuration.

B:

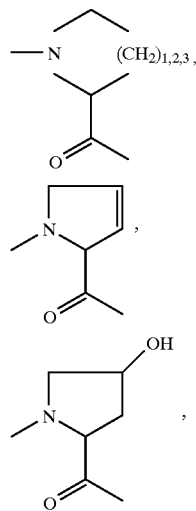

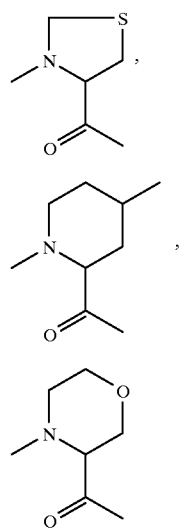

The B fragments preferably have the L configuration.

$R^9$: is Cl, Br, $NO_2$, $R^{15}O$, $R^{15}OOC$, $R^{15}OCH_2$, $R^{15}NH$, $R^{15}CONH$ or $R^{15}OOCCH_2O$, where $R^{15}$ is H, $C_1$–$C_6$-alkyl, benzyl or phenyl, $R^{10}$: is H, $C_1$–$C_4$-alkyl or $R^{15}O$.

Particularly preferred substituents R and fragments A and B have the following meanings:

$R^1$: HO, $CH_3$, $CH_3$–$CH_2$, $CH_3$—$(CH_2)_3$, $CF_3$—$CH_2$, phenyl, benzyl, phenethyl, pyridyl, $(CH_3)_2N$, $CH_3$—NH, $NH_2$ and piperidinyl, A: cyclohexylglycine or cyclohexylalanine, tetrahydro-4-pyranylglycine, tetrahydro-4-pyranylvaline, dicyclohexyl- or diphenylalanine or phenylalanine, it being possible for the phenyl rings to be substituted by up to 3 identical or different $CH_3O$, $CH_3$, HO, F or Cl radicals, serine or tert-butylserine.

The amino acids preferably have the D configuration.

B:

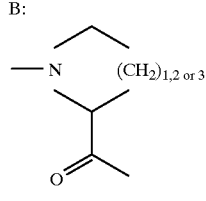

or

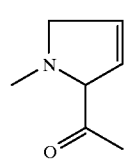

The B fragments preferably have the L configuration.

$R^9$: Cl, $CH_3O$ or HO $R^{10}$: H, $CH_3$ or $CH_3O$

Ic:
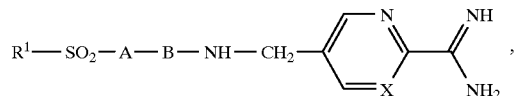

Id:
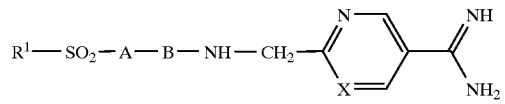

and

Ie:
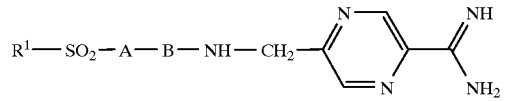

The meanings of the substituent $R^1$, the fragments A and B and X herein are as follows:

$R^1$: OH, $C_1$–$C_{10}$-alkyl, $CF_3CH_2$, phenyl, naphthyl, phenyl-$C_1$–$C_4$-alkyl (especially benzyl and phenethyl), naphthyl-$C_1$–$C_4$-alkyl, pyridyl, isoquinolyl, $NH_2$, $C_1$–$C_4$-mono- or dialkylamino, piperidinyl.

A: glycine, alanine, valine, leucine, isoleucine, phenyl- or cyclohexylglycine, phenyl- or cyclohexylalanine, tetrahydropyranylglycine, tetrahydropyranylvaline, diphenyl- or dicyclohexylalanine, it being possible for phenyl rings present in the residues to be substituted by up to three identical or different $C_1$–$C_4$-alkyl, O—$C_1$–$C_4$-alkyl, OH, F, Cl or $COOR^6$ radicals, aspartic acid, glutamic acid, asparagine, glutamine, the nitrogen atom possibly carrying, if required, one or two alkyl groups or being part of a $C_4$–$C_8$ ring, serine, homoserine, threonine, it being possible for the carboxyl or hydroxyl group to be esterified or etherified by a $C_1$–$C_8$-alkyl radical.

The amino acids A preferably have the D configuration.

B:
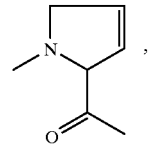

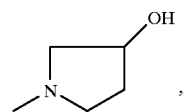

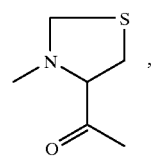

-continued

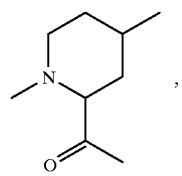

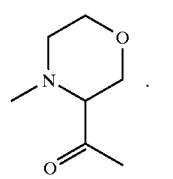

The B fragments preferably have the L configuration.

X: CH or N.

Particularly preferred meanings for the substituent $R^1$, the fragments A and B and X are as follows:

$R^1$: HO, $CH_3$, $CH_3$—$CH_2$, $CH_3$—$(CH_2)_3$, $CF_3$—$CH_2$, phenyl, benzyl, phenethyl, pyridyl, $(CH_3)_2N$, $CH_3$—NH, $NH_2$ and piperidinyl, A: cyclohexylglycine or cyclohexylanine [sic], tetrahydro-4-pyranylglycine, tetrahydro-4-pyranylvaline, dicyclohexyl- or diphenylalanine or phenylalanine, it being possible for the phenyl rings to be substituted by up to 3 identical or different $CH_3O$, $CH_3$, HO, F or Cl radicals, serine or tert-butylserine.

The amino acids preferably have the D configuration.

B:
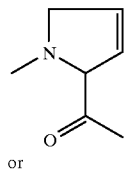

or

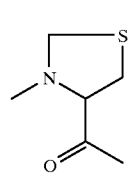

The B fragments preferably have the L configuration.

X: CH or N or the substituents R, the fragments A and B and X in the compounds Ic, Id and Ie have the following meanings:

$R^1$: OH, $C_1$–$C_{10}$-alkyl, $CF_3CH_2$, phenyl, naphthyl, phenyl-$C_1$–$C_4$-alkyl (especially benzyl and phenethyl), naphthyl-$C_1$–$C_4$-alkyl, pyridyl, isoquinolyl, $NH_2$, $C_1$–$C_4$-mono- or dialkylamino, piperidinyl.

A: cyclohexylglycine or cyclohexylanine [sic], tetrahydropyranylglycine, tetrahydropyranylvaline, diphenyl- or dicyclohexylalanine, phenylalanine which is substituted by 2 or 3 identical or different radicals from the group of $CH_3O$, $CH_3$, HO, F or Cl, or serine or tert-butylserine. The amino acids A preferably have the D configuration.

B:

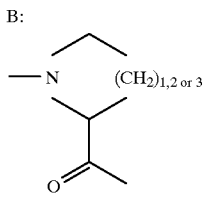

The B fragment preferably has the L configuration.
X: CH or N

If:

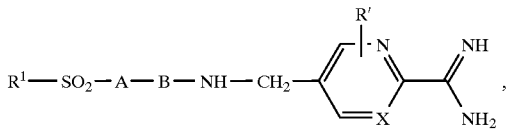

Ig:

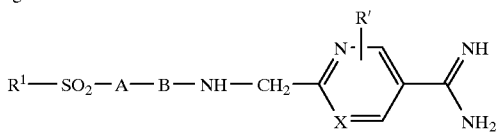

The substituents R, the fragments A and B and X herein have the following meanings:

$R^1$: OH, $C_1-C_{10}$-alkyl, $CF_3CH_2$, phenyl, naphthyl, phenyl-$C_1-C_4$-alkyl (especially benzyl and phenethyl), naphthyl-$C_1-C_4$-alkyl, pyridyl, isoquinolyl, $NH_2$, $C_1-C_4$-mono- or dialkylamino, piperidinyl.

A: glycine, alanine, valine, leucine, isoleucine, phenyl- or cyclohexylglycine, phenyl- or cyclohexylalanine, tetrahydro-4-pyranylglycine, tetrahydro-4-pyranylvaline, α-methylcyclohexylalamine [sic], diphenyl- or dicyclohexylalanine, it being possible for phenyl rings present in the residues to be substituted by up to three identical or different $C_1-C_4$-alkyl, O—$C_1-C_4$-alkyl, OH, F, Cl or $COOR^6$ radicals, aspartic acid, glutamic acid, asparagine, glutamine, the nitrogen atom possibly carrying, if required, one or two alkyl groups or being part of a $C_4-C_8$ ring, serine, homoserine, threonine, it being possible for the carboxyl or hydroxyl group to be esterified or etherified by a $C_1-C_8$-alkyl radical. The amino acids preferably have the D configuration.

B:

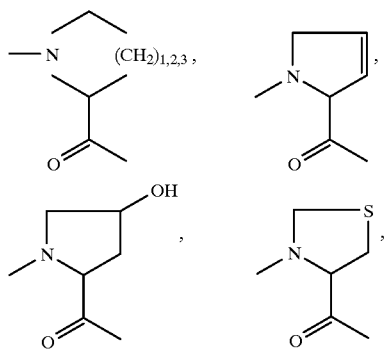

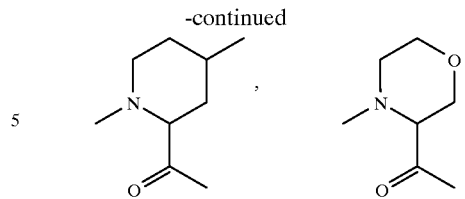

The B fragments are preferably in the L configuration.
R': $CH_3$ or $CH_3O$
X: CH or N The following substances may be specifically mentioned:
$MeSO_2$-(D)-α-Me-Cha-Pro-NH-(2-MeO)-4-amb
$EtSO_2$-(D,L)-Cog-Pro-NH-(2-MeO)-4-amb
$EtSO_2$-D-(3,4-Dimethoxy)Phe-Pro-NH-(2-MeO)-4-amb
$MeSO_2$-(D,L)-(1-Tetralinyl)Gly-Pro-NH-(2-MeO)-4-amb
$MeSO_2$-(D,L)-Dpa-Pro-NH-(2-MeO)-4-amb
$MeSO_2$-(D,L)-(5-Dibenzosuberyl)Gly-Pro-NH-(2-MeO)-4-amb
$EtSO_2$-D-(4-Methoxy)Phe-Pro-NH-(2 MeO)-4-amb
$MeSO_2$-(D,L)-(3,4,5-Trimethoxy)Phe-Pro-NH-(2-MeO)-4-amb
$CF_3SO_2$-D-(4-Chloro)Phe-Pro-NH-(2-MeO)-4-amb
$CF_3SO_2$-(D,L)-($Me_3Si$)Ala-Pro-NH-(2-MeO)-4-amb
$MeSO_2$-(D)-Chg-Pro-NH-(2-MeO)-4-amb
$CF_3CH_2SO_2$-(D)-Chg-Pro-NH-(2-MeO)-4-amb
$MeSO_2$-(D)-Phe-Aze-NH-(2-MeO)-4-amb
$MeSO_2$-(D)-(tert-Butyl)Ser-Pro-NH-(2-MeO)-4-amb
$MeSO_2$-(D)-Cha-Pro-NH-(2-MeO)-4-amb
$Bz$-$SO_2$-(D)-Cha-Pro-NH-(2-MeO)-4-amb
n-Bu-$SO_2$-(D)-Cha-Pro-NH-(2-MeO)-4-amb
HO—$SO_2$-(D)-Chg-Pro-NH-(2-MeO)-4-amb
$H_2N$—$SO_2$-(D)-Chg-Pro-NH-(2-MeO)-4-amb
$H_2N$—$SO_2$-(D)-Chg-Pro-NH-(2-MeO)-4-amb
HOOC—$CH_2$—$CH_2$—$SO_2$-(D)-Chg-Pro-NH-(2-MeO)-4-amb
2-Naphth.-$SO_2$-(D)-Phe-Pro-NH-(2-MeO)-4-amb
$MeSO_2$-(D,L)-(β-Phenyl)Pro-Pro-NH-(2-MeO)-4-amb
$MeSO_2$-(D)-Chg-Aze-NH-(2-MeO)-4-amb
$MeSO_2$-(D)-Chg-Pic-NH-(2-MeO)-4-amb
$MeSO_2$-(D)-Chg-Hyp-NH-(2-MeO)-4-amb
$MeSO_2$-(D)-Chg-Pyr-NH-(2-MeO)-4-amb
$EtSO_2$-(D)-Chg-(N-cyclopropyl)Gly-NH-(2-MeO)-4-amb
$MeSO_2$-(D)-Chg-1-Tic-NH-(2-MeO)-4-amb
$MeSO_2$-(D)-Chg-2-Ind-NH-(2-MeO)-4-amb
$MeSO_2$-(D)-Chg-2-Phi-NH-(2-MeO)-4-amb
$EtSO_2$-(D)-Chg-(Cyclo)Leu-NH-(2-MeO)-4-amb
Pro-$SO_2$-(D)-Chg-Pro-NH-(2-iPrO)-4-amb
Ph-$SO_2$-(D)-Chg-Pro-NH-(2-OH)-4-amb
$MeSO_2$-(D)-Chg-Pro-NH-(2-$OCH_2$-COOH)-4-amb
$MeSO_2$-(D)-Chg-Pro-NH-(2-NH-COMe)-4-amb
$MeSO_2$-(D)-Chg-Pro-NH-(2-$NH_2$)-4-amb
$EtSO_2$-(D)-Chg-Pro-NH-(2-COOH)-4-amb
$MeSO_2$-(D)-Chg-Pro-NH-(2-COOMe)-4-amb
$MeSO_2$-(D)-Chg-Pro-NH-(2-$CH_2OH$)-4-amb
$EtSO_2$- (D) -Chg-Pro-NH-(2-Cl)-4-amb
HO—$SO_2$-(D)-Chg-Pro-NH-(2-Br)-4-amb
$H_2N$—$SO_2$-(D)-Chg-Pro-NH-(2,6-Dimethoxy)-4-amb
$MeSO_2$-(D)-Chg-Pro-NH-(2,3-Dimethoxy)-4-amb
$EtSO_2$-(D)-Chg-Pro-NH-(3-MeO)-4-amb
$HOSO_2$-(D)-Chg-Pro-NH-(3-OH)-4-amb
$CF_3SO_2$-(D)-Chg-Pro-NH-(3-iPrO)-4-amb
$MeSO_2$-(D)-Chg-Pro-NH-(3-Cl)-4-amb
$EtSO_2$-(D)-Chg-Pro-NH-(4-am)-napme
$MeSO_2$-(D)-Chg-Pro-NH-4-amb(Me)
$MeSO_2$-(D)-Chg-Pro-NH-4-amb(COOH)

MeSO$_2$-(D)-Chg-Pro-NH-4-amb(COOMe)
MeSO$_2$-(D)-Phe-Pro-NH-4-amb(CH$_2$OH)
MeSO$_2$-(D)-Phe-Pro-NH-4-amb(CO—CH$_2$Ph)
MeSO$_2$-(D)-Chg-Pro-NH-4-amb(CO—CF$_3$)
MeSO$_2$-(D)-Chg-Pro-NH-4-amb(CHO)
MeSO$_2$-(D)-Chg-Pro-NH-4-amb(COCH$_2$OH)
MeSO$_2$-(D)-Chg-Pro-NH-4-amb(COCONHCH$_3$)
MeSO$_2$-(D)Phe-Pro-NH-(6-am)-3-pic
MeSO$_2$-(D)Phe-Pro-NH-(5-am)-2-pic
MeSO$_2$-(D)Phe-Pro-NH-(2-am-5-pyrim)methyl
MeSO$_2$-(D)Phe-Pro-NH-(5-am-2-pyrim)methyl
MeSO$_2$-(D)Phe-Pro-NH-(6-am-2-MeO)-3-pic
MeSO$_2$-(D)Phe-Pro-NH-(2-am-5-pyraz)methyl
EtSO$_2$-(D)Phe-Pro-NH-(6-am-2-F)-3-pic
CF$_3$—CH$_2$—SO$_2$-(D)Phe-Pro-NH-(6-am-2-OH)-3-pic
n-BuSO$_2$-(D)-Phe-Pro-NH-(6-am-2-BzO)-3-pic
n-BuSO$_2$-(D)-Phe-Pro-NH-(6-am-2-OH)-3-pic
n-Octyl-SO$_2$-(D)-Phe-Pro-NH-(6-am-2-i-PrO)-3-pic
Benzyl-SO$_2$-(D)-Phe-Pro-NH-(6-am-2-OCH$_2$COOM)e-3-pic
i-Propyl-SO$_2$-(D)Phe-Pro-NH-(5-am-6-Cl)-2-pic
Phenyl-SO$_2$-(D)Phe-Pro-NH-(5-am-3-MeO)-2-pic
2-Naphthyl-SO$_2$-(D)Phe-Pro-NH-(5-am-3-OH)-2-pic
3-Pyridyl-SO$_2$-(D)Phe-Pro-NH-(5-am-3-Me)-2-pic
2-Thienyl-SO$_2$-(D)Phe-Pro-NH-(5-am-4-Me)-2-pic
N-Piperidinyl-SO$_2$-(D)Phe-Pro-NH-(5-am-3-MeO)-2-pic
H$_2$N—SO$_2$-(D)Phe-Pro-NH-(5-am-4,6-Cl$_2$-2-pyrim)methyl
Me$_2$N—SO$_2$-(D)Phe-Pro-NH-(2-am-4,6-(OH)$_2$-5-pyrim)methyl
EtHN-SO$_2$-(D)Phe-Pro-NH-(2-am-4,6-Cl$_2$-5-pyrim)methyl
MeSO$_2$-(D)Phe(4-OMe)-Pro-NH-(2-am-4,6-Me$_2$-5-pyrim)methyl
MeSO$_2$-(D)Phe(3-OMe)-Pro-NH-(5-am-4,6-(OH)$_2$-2-pyrim)methyl
MeSO$_2$-(D)Phe(4-Cl)-Pro-NH-(5-am-4,6-Me$_2$-2-pyrim)methyl
MeSO$_2$-(D)Cha-Pro-NH-(6-am)-3-pic
MeSO$_2$-(D)Cha-Pyr-NH-(6-am)-3-pic
MeSO$_2$-(D)Cha-Pro-NH-(5-am)-2-pic
MeSO$_2$-(D)Cha-Pro-NH-(2-am-5-pyrim)methyl
MeSO$_2$-(D)Cha-Pro-NH-(5-am-2-pyrim)methyl
MeSO$_2$-(D)Cha-Pro-NH-(6-am-2-Me)-3-pic
MeSO$_2$-(D)Cha-Pro-NH-(6-am-2-MeO)-3-pic
MeSO$_2$-(D)Cha-Pro-NH-(6-am-2-Cl)-3-pic
MeSO$_2$-(D)Cha-Pro-NH-(2-am-4,6-(MeO)$_2$-5-pyrim)methyl
MeSO$_2$-(D)Cha-Pro-NH-(5-am-4,6-(MeO)$_2$-2-pyrim)methyl
MeSO$_2$-(D)Cha-Pro-NH-(2-am)-5-pyraz
MeSO$_2$-(D)Chg-Pro-NH-(6-am)-3-pic
MeSO$_2$-(D)Chg-Pyr-NH-(6-am)-3-pic
MeSO$_2$-(D)Chg-Pro-NH-(5-am)-2-pic
MeSO$_2$-(D)Chg-Pro-NH-(2-am-5-pyrim)methyl
MeSO$_2$-(D)Chg-Pro-NH-(5-am-2-pyrim)methyl
MeSO$_2$-(D)Chg-Pro-NH-(6-am-2-Me)-3-pic
MeSO$_2$-(D)Chg-Pro-NH-(6-am-2-MeO)-3-pic
MeSO$_2$-(D)Chg-Pro-NH-(6-am-2-Cl)-3-pic
MeSO$_2$-(D)Chg-Pro-NH-(2-am-4,6-(MeO)$_2$-5-pyrim)methyl
MeSO$_2$-(D)Chg-Pro-NH-(5-am-4,6-(MeO)$_2$-2-pyrim)methyl
MeSO$_2$-(D)Dpa-Pro-NH-(6-am-3)-pic
MeSO$_2$-(D)Dpa-Pro-NH-(2-am-5-pyrim)methyl
MeSO$_2$-(D)Dpa(4,4'-MeO)-Pro-NH-(6-am)-3-pic
MeSO$_2$-(D)Dpa(4,4'-Cl$_2$)-Pro-NH-(6-am)-3-pic
MeSO$_2$-(D,L)Phg(3,4-Cl$_2$)-Pro-NH-(5-am)-2-pic
MeSO$_2$-(D,L)Phg(3,4-Cl$_2$)-Pro-NH-(5-am)-2-pyrim)methyl
MeSO$_2$-(D)Tbg-Pro-NH-(6-am-2-MeO)-3-pic
MeSO$_2$-(D)Asp(OH)-Pro-NH-(2-am-4,6-Cl$_2$-5-pyrim)methyl
MeSO$_2$-(D)Asp(OMe)-Pro-NH-(2-am-5-pyrim)methyl
MeSO$_2$-(D)Asp(OMe)-Pro-NH-(6-am-2-Me)-3-pic
MeSO$_2$-(D)Asp(OtBu)-Pro-NH-(6-am)-3-pic
MeSO$_2$-(D)Asp(OtBu)-Pro-NH-(5-am-2-pyrim)methyl
MeSO$_2$-(D)Phe-Aze-Pro-NH-(5-am)-2-pic
MeSO$_2$-(D)Phe-Aze-Pro-NH-(2-am-4,6-(MeO)$_2$-5-pyrim)methyl
MeSO$_2$-(D)Phe-Pip-Pro-NH-(6-am)-3-pic
MeSO$_2$-(D)Phe-Pip-Pro-NH-(2-am-5-pyrim)methyl
1-Naphthyl-SO$_2$-Gly-Pro-NH-(5-am-)2-pic
1-Naphthyl-SO$_2$-Gly-Pro-NH-(6-am-2-Me)-3-pic
HOOC—(CH$_2$)$_3$—SO$_2$-(D)Chg-Pro-NH-(6-am)-3-pic
HOOC—(CH$_2$)$_3$—SO$_2$-(D)Chg-Pro-NH-(5-am)-2-pic
MeSO$_2$-(D)Ser(t-Bu)-Pro-NH-(6-am)-3-pic
MeSO$_2$-(D)Ser(t-Bu)-Pro-NH-(5-am)-2-pic
HO$_3$S-(D)Chg-Pro-NH-(6-am)-3-pic
MeSO$_2$-TMSiA-Pro-NH-(6-am)-3-pic The following substances may be mentioned as preferred:
1. MeSO$_2$-(D)-(4-Methoxy)Phe-Pro-NH-(2-MeO)-4-amb
2. MeSO$_2$-(D)-Chg-Pro-NH-4-amb(Me)
3. MeSO$_2$-(D)-Cha-Pro-NH-(2-MeO)-4-amb
4. MeSO$_2$-(D,L)-Dpa-Pro-NH-(2-MeO)-4-amb
5. MeSO$_2$-(D)-Phe-Pro-NH-(6-am)-3-pic
6. MeSO$_2$-(D)-Chg-Pro-NH-(6-am)-3-pic
7. MeSO$_2$-(D)-Chg-Pro-NH-(5-am)-2-pic
8. MeSO$_2$-(D)-Cha-Pyr-NH-(6-am)-3-pic
9. MeSO$_2$-(D)-Chg-Pyr-NH-(6-am)-3-pic
10. HOOC—CH$_2$—SO$_2$-(D)-Cha-Pro-NH-(6-am)-3-pic List of abbreviations:
AIBN: Azobisisobutyrodintrile [sic]
am: Amidino
Ala: Alanine
4-amb: 4-Amidinobenzyl
Asp: Aspartic acid
Aze: Azetidinecarboxylic acid
Boc: tert-Butyloxycarbonyl
Bz: Benzyl
Cbz: Benzyloxycarbonyl
Cha: Cyclohexylalanine
Chg: Cyclohexylglycine
Cog: Cyclooctylglycine
Cpa: Cyclopentylalanine
(Cyclo)Leu: 1-Aminocyclohexanecarboxylic acid
DCM: Dichloromethane
Gly: Glycine
Hyp: Hydroxyproline
2-Ind: 2 Indolinecarboxylic [sic] acid
Leu: Leucine
napme: Naphthylmethyl
NBS: N-Bromosuccinimide
Ph: Phenyl
Phe: Phenylalanine
2-Phi: 2-Perhydroindolecarboxylic acid
pic: Picolyl
Pip: Pipecolic acid
Pro: Proline
Pyr: 3,4-Pyrroline-2-carboxylic acid
pyrim: Pyrimidyl
pyraz: Pyrazinyl
Tbg: tert-Butylglycine 1-Tic: 1-Tetrahydroisoquinolinecarboxylic acid
3-Tic: 3-Tetrahydroisoquinolinecarboxylic acid
TMSiA: Trimethylsilylalanine 4-amb($R^{13}$) is the structure

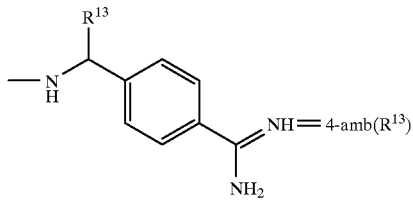

The invention furthermore relates to the compounds of the formulae VII, VIII, IX and X

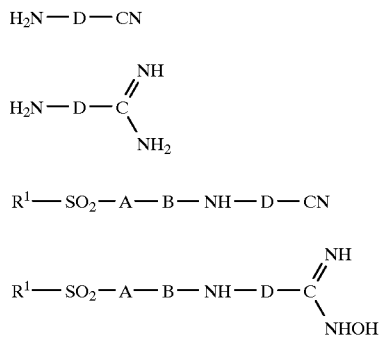

where $R^1$, A, B and D have the stated meanings, and where the amidine functionality in formula VIII and in formula I can be in mono- or diprotected form. The intermediates are novel, are used for preparing the compounds I and are valuable building blocks for synthesizing serine protease inhibitors.

The structural fragment of the formula XI

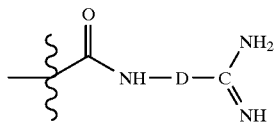

is novel and is valuable as constituent of serine protease inhibitors and, in particular, of thrombin inhibitors.

The compounds of the formula I may be used as such or in the form of their salts with physiologically tolerated acids. Examples of such acids are: hydrochloric acid, citric acid, tartaric acid, lactic acid, phosphoric acid, methanesulfonic acid, acetic acid, formic acid, maleic acid, fumaric acid, maleic [sic] acid, succinic acid, hydroxysuccinic acid, sulfuric acid, glutaric acid, aspartic acid, pyruvic acid, benzoic acid, glucuronic acid, oxalic acid, ascorbic acid and acetylglycine.

The amidine functionality in the compounds I can be mono- or diprotected by an amino protective group. Cbz and BOC [sic] groups are particularly suitable as protective group. The same applies to the amidine functionality in the compounds VIII.

The compounds I can be prepared starting from the α-amino acid H—A—OH or from the N-protected cyclic amino acid B—OH as shown in reaction schemes I and II.

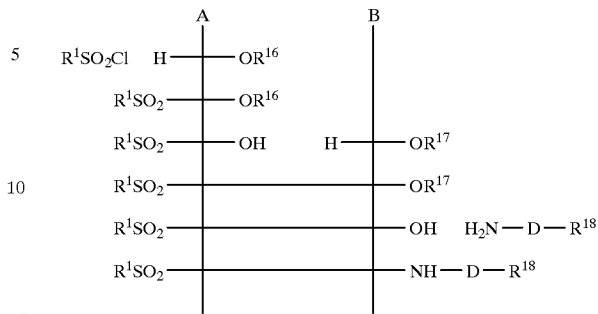

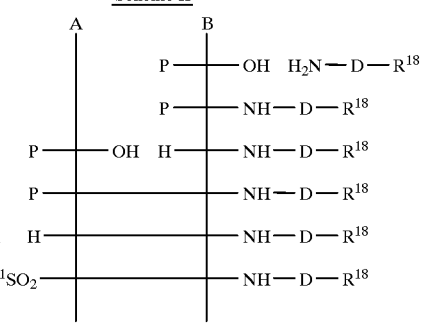

In the above reaction schemes, $R^{16}$ is H or $C_1$–$C_4$-alkyl, $R^{17}$ is $C_1$–$C_4$-alkyl, preferably methyl or t-butyl, $R^{18}$ is CN or

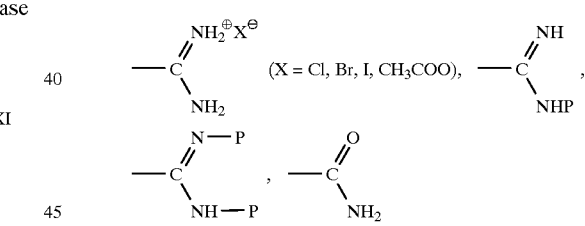

and P is a protective group, preferably t-butoxycarbonyl (Boc) or benzyloxycarbonyl (Cbz).

Alternatively, the protected amino acids P—A—OH and H—B—$OR^{17}$ can be coupled to give the dipeptide P—A—B—$OR^{17}$ and then be reacted, after elimination of P, with $R^1SO_2Cl$ or, after elimination of $R^{17}$, with compounds of the formula VII or VIII, with the reaction sequence being arbitrary.

$R^1$—$SO_2$—A—OH can also be coupled directly with

to give the final product I or intermediate VII or IX.

If amidine-containing intermediates are used in protected form in the above reaction sequences, the protective group(s) are eliminated at the final stage.

If R[18] is an amide, [lacuna] can be, after linkage to give

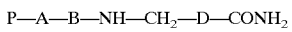
P—A—B—NH—CH₂—D—CONH₂ or

R¹—SO₂—A—B—NH—CH₂—D—CONH₂, converted to the nitrile and therefrom further to the amidine.

The required coupling reactions are carried out under standard conditions of peptide chemistry (see M. Bodansky, A. Bodansky "The Practice of Peptide Synthesis", Springer Verlag, (1084 [sic]).

Boc protective groups are eliminated with HCl/dioxane or CF₃COOH/methylene chloride, and Cbz protective groups are eliminated by hydrogenolysis or with HF. Ester functionalities are hydrolyzed with NaOH or LiOH in an alcoholic solvent such as methanol or ethanol. t-Butyl esters are hydrolyzed with acids, eg. CF₃COOH.

The reaction with the sulfonyl chlorides R¹—SO₂Cl in the presence of an organic base such as triethylamine, pyridine or N,N-diisopropylethylamine takes place in organic solvents such as CH₂Cl₂, THF or DMF. In the case of free carboxyl groups, the reaction is carried out in the presence of aqueous alkali metal hydroxide or carbonate solutions.

The amidines are prepared from the nitrile precursors by the classical Pinner synthesis (R. Roger and D. G. Neilson, Chem. Rev. 61 (1961) 179) or, preferably, by a modified Pinner synthesis which takes place via imino thioester salts as intermediates (H. Vieweg et al., Pharmazie 39 (1984) 226). Catalytic hydrogenation of N-hydroxyamidines, which are obtainable by addition of hydroxylamine onto the cyano group, with Raney Ni or Pd/C in alcoholic solvents likewise results in amidines (B. J. Broughton et al., J. Med. Chem. 18 (1975) 1117).

The novel compounds can be used for the therapy and prophylaxis of thrombin-dependent thromoembolic events such as deep vein thromboses, pulmonary embolisms, myocardial or cerebral infarcts and unstable angina, also for the therapy of disseminated intravascular coagulation (DIC). They are furthermore suitable for combination therapy with thrombolytics such as streptokinase, urokinase, prourokinase, t-PA, APSAC and other plasminogen activators to shorten the reperfusion time and prolong the reocclusion time.

Further uses are the prevention of thrombin-dependent early reocclusion and later restenosis after percutaneous transluminal coronary angioplasty, prevention of thrombin-induced proliferation of smooth muscle cells, prevention of the accumulation of active thrombin in the CNS (eg. in Alzheimer's disease), control of tumors and prevention of mechanisms leading to adhesion and metastasis of tumor cells.

Their particular advantage is that they are effective even after oral administration.

The compounds according to the invention can be administered in a conventional way orally or parenterally (subcutaneously, intravenously, intramuscularly, intraperitoneally, rectally). Administration can also take place with vapors or sprays through the nasopharyngeal space.

The dosage depends on the age, condition and weight of the patient and on the mode of administration. As a rule, the daily dose of active ingredient per person is about 10–2000 mg on oral administration and about 1–200 mg on parenteral administration. This dose can be given in 2 to 4 single doses or once a day in depot form.

The novel compounds can be used in conventional solid or liquid pharmaceutical forms, eg. as uncoated or (film-)coated tablets, capsules, powders, granules, suppositories, solutions, ointments, creams or sprays. These are produced in a conventional manner. The active ingredients can for this purpose be processed with conventional pharmaceutical aids such as tablet binders, fillers, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1978). The forms obtained in this way normally contain the active ingredient in an amount of from 0.1 to 99 percent by weight.

EXAMPLE 1

N-Methylsulfonyl-(D)-phenylalanyl-proline 2-methoxy-4-amidinobenzylamide acetate (a) 3-Nitro-4-methylbenzonitrile 399 g (2.56 mol) of 4-methylbenzonitrile were added over the course of 90 min into 1 l of fuming nitric acid at –10° C. 1 h after the addition, the mixture was poured into 2.5 l of ice-water, whereupon a solid precipitated and was separated off on a suction filter funnel and washed to neutral pH with water. The yield was 363 g (88%). ¹H-NMR (CDCl₃; δ in ppm): 8.3 (d,1H); 7.8 (dd, 1H); 7.5 (dd, 1H); 2.7 (s, 3H)

(b) 3-Amino-4-methylbenzonitrile 120 g of 3-Nitro-4-methylbenzonitrile were suspended in 1.2 l of EtOH and hydrogenated in the presence of 7 g of Pd/C (10%) with 50 l of hydrogen at room temperature. After removal of the catalyst, the solvent was stripped off. 95 g of pure product were obtained (97%). ¹H-NMR (DMSO-d⁶; δ in ppm): 7.1 (dd, 1H); 6.90 (d, 1H); 6.85 (dd, 1H); 5.35 (s, 2H, NH2 [sic]); 2.15 (s, 3H)

(c) 3-Hydroxy-4-methylbenzonitrile

A solution of 49.2 g (0.72 mol) of NaNO₂ in 217 ml of water was added dropwise to 85 g (0.72 mol) of 3-amino-4-methylbenzonitrile in 1.8 l of 6N HCl at 0–5° C. over the course of 0.5 h. The mixture was then stirred at 0–5° C. for a further 30 min and subsequently at the boiling point for 1 h. After the solution had cooled, the product was extracted with ethyl acetate and, from this, in the form of the phenolate with ice-cooled 5 N NaOH. The aqueous phase was then acidified to pH 3 with 6N HCl, and the product was extracted with ethyl acetate. 41 g (43%) were obtained. ¹H-NMR (DMSO-d⁶; δ in ppm): 10.3 (s, OH); 7.25 (dd, 1H); 7.15 (d, 1H); 7.1 (dd, 1H); 2.20 (s, 3H)

(d) 3-Methoxy-4-methylbenzonitrile 15 g (0.11 mol) of 3-hydroxy-4-methylbenzonitrile dissolved in 30 ml of DMF were added dropwise to a suspension of 0.11 mol of NaH in 30 ml of DMF, and the mixture was stirred until no further H₂ evolution was observed. Then 10.6 ml (0.17 mol) of methyl iodide were added dropwise, and the mixture was stirred at room temperature for 1 h. The solution was poured into ice-water, and the product was extracted with ether/ethyl acetate 7:1. After the solvent had been stripped off, the product began to crystallize slowly. 14.8 g (89%) were obtained. ¹H-NMR (CDCl₃; δ in ppm): 7.2 (m, 2H); 7.02 (s, 1H); 3.85 (s, 3H); 2.25 (s, 3H).

(e) 4-Bromomethy-3-methoxybenzonitrile [sic]

14.7 g (0.1 mol) of 3-methoxy-4-methylbenzonitrile were dissolved in 210 ml of 1,2-dichloroethane, brominated with 19.1 g (0.11 mol) of NBS in portions over the course of 1 h in the presence of catalytic amounts of azobisisobutyronitrile at 82° C. and, after the addition was complete, stirred at 82° C. for a further 30 min. After addition of n-heptane, precipitated succinimide was removed, and the solvent was stripped off. The yield was 18.5 [lacuna] (82%). $^1$H-NMR (DMSO-d$^6$; δ in ppm): 7.60 (dd, 1H); 7.50 (d, 1H); 7.40 (dd, 1H); 4.68 (s, 2H); 3.96 (s, 3H)

(f) 4-Phthalimidomethyl-3-methoxybenzonitrile 24.4 g (108 mol [sic]) of 4-bromomethyl-3-methoxybenzonitrile, dissolved in 125 ml of DMF, and 20.0 g of potassium phthalimide were stirred at room temperature for 24 h and then at 50° C. for 1 h. The mixture was poured into water, whereupon the product precipitated as solid. 21.5 g (68%) were obtained. $^1$H-NMR (DMSO-d$^6$; δ in ppm): 7.9 (m, 4H); 7.5 (d, 1H); 7.35–7.25 (m, 2H); 7.78 (s, 2H); 3.92 (s, 3H)

(g) 4-Aminomethyl-3-methoxybenzonitrile 10.6 ml of hydrazine hydrate were added to 21.2 g (73 mmol) of 4-phthalimidomethyl-3-methoxybenzonitrile dissolved in 290 ml of THF, and the mixture was stirred at room temperature for 20 h. Then 180 ml of 2H [sic] HCl were added dropwise and, after 1.5 h, the solvent was completely stripped off. The residue was taken up in MTBE, extracted with 1N HCl, adjusted to pH 9–10 with 2N NaOH and extracted with methylene chloride. 8.0 g (68%) of product were obtained. $^1$H-NMR (DMSO-d$^6$; δ in ppm): 7.55 (dd, 1H); 7.40 (dd, 1H; 7.37 (d, 1); 3.85 (s, 3H); 3.70 (s, 2H); 2.5–1.6 (NH$_2$).

(h) Boc-proline 4-cyano-2-methoxybenzylamide 16.0 g of Boc-proline (50 mmol), dissolved in 80 ml of THF, were stirred with 5.7 g of hydroxysuccinimide and 10.2 g of DCC in methylene chloride at 0° C. for 30 min. Then 8.0 g (50 mmol) of 4-aminomethyl-3-methoxybenzenenitrile [sic] dissolved in 50 ml of THF were added dropwise at 0° C., and the mixture was stirred at room temperature for 20 h. The solid was filtered off, the filtrate was mixed with the same volume of ethyl acetate and washed with cooled 5% strength NaHSO$_4$ solution and saturated NaCl solution. 11.5 g (65%) of product were obtained. $^1$H-NMR (DMSO-d$^6$; δ in ppm): 8.38 (m, NH); 7.50–7.35 (m, 3H); 4.40–4.05 (m, 3H, N—CH$_2$—Ar/N—CH—CO); 3.87 (s, OCH$_3$); 3.50–3.25 (m, 2H, N—CH$_2$); 2.2.5–2.00 [sic] (m, 1H); 1.90–1.65 (m, 3H); 1.40 and 1.30 (2s; 9H)

(i) Proline 2-methoxy-4-cyanobenzylamide 11.4 g (31.7 mmol) of Boc-proline 2-methoxy-4-cyanobenzylamide were dissolved in 130 ml of methylene chloride and, at 0–5° C., saturated with HCl [sic]. After 2 h the Boc group had been completely eliminated. The solvent was removed under reduced pressure, and the product was used without further purification in the next reaction. $^1$H-NMR (DMSO-d$^6$; δ in ppm): 10.25 (s, 1H); 8.60 (s, 1H); 7.50 (d, 1H; 7.42 (dd, 1H); 7.39 (d, 1); 4.40–4.20 (m, 3H); 3.88 (s, 3H); 3.20 (m, 2H); 2.35 (m, 1H); 2.00–1.80 (m, 3H)

(j) Boc-(D)-4-methoxyphenylalanylproline 2-methoxy-4-cyanobenzylamide 1.55 g (5.25 mmol) of Boc-(D)-Phe-(4-OMe)-OH, 3.9 ml of diisopropylethylamine and 1.55 g (5.25 mmol) of proline 2-methoxy-4-cyanobenzylamide hydrochloride were mixed at −5° C. with 4.4 ml (5.9 mmol) of propanephosphonic anhydride (50% strength in ethyl acetate) in 35 ml of methylene chloride and stirred at 0° C. for 1 h. The reaction mixture was washed successively with 1 N NaOH, 1 N HCl and saturated brine and dried over Na$_2$SO$_4$. The solvent was stripped off to leave 2.4 g of a solid. $^1$H-NMR (DMSO-d$^6$; δ in ppm): 8.72 and 7.87 (t, 2H); 7.42 (1H); 7.35 (m, 3H); 7.15 (d, 2H); 6.85 (d, 2H); 7.00+6.70 (2 d) 1H; 4.40–4.10 (m, 4H); 3.85 (s, 3H; 3.70 (s, 3H); 3.05–2.55 (m, 4H); 1.95–1.55 (m, 4H); 1.2 (s, 9H)

(k) (D)-4-Methoxyphenylalanylprolin 2-methoxy-4-amidinobenzylamide dihydrochloride The nitrile was converted by known processes (DE 4121947) via the thioamide stage into the amidine. Starting from the nitrile, 2.2 g of the thioamide were obtained. $^1$H-NMR (DMSO-d$^6$; δ in ppm): 9.85 (s, 1H); 9.45 (s, 1H); 8.65/7.85 (2 t, 1H); 7.55–6.65 (m, 7H, Ar—H); 4.40–4.10 (m, 4H); 3.86/3.85 (2 s, 3H); 3.71/3.70 (2 s, 3H); 3.05–2.60 (m, 4H); 2.10–1.55 (m, 4H); 1.35–1.10 (s, 9H)

Starting from 2.2 g of the thioamide and after reaction with methyl iodide and methanolic ammonia solution and purification by column chromatography on silica gel (mobile phase: DCM/MeOH 9:1), 1.7 g of the amidine were obtained as hydroiodide. $^1$H-NMR (DMSO-d$^6$; δ in ppm): 9.28 (s, 2H); 8.87 (s, 2H); 8.75/7.95 (st, 1H); 7.40–6.65 (m, 7H, Ar-H); 4.45–4.10 (m, 4H); 3.90 (s, 3H); 3.70 (s, 3H); 3.7–3.4/3.0–2.6 (m, 4H); 1.95–1.55 (m, 4H); 1.30/1.22 (2 s, 9H).

The amidine hydroiodide was converted into the amidine hydrochloride on an IRA 420 ion exchanger, then dissolved in 50 ml of methylene chloride and saturated with HCl [sic] at 0–5° C. After stirring for 1 h, the solvent was stripped off. 1.0 g of the amidine was obtained as dihydrochloride. FAB-MS (M$^+$) 453

$^1$H-NMR (DMSO-d$^6$, δ in ppm): 9.50 (5(broad) [sic], 2H), 9.25 (s(broad), 2H), 8.85–8.65 (broad signal, 3H); 7.40 (s, 1H), 7.35 (d, 1H), 7.30 (d, 1H), 7.15 (d, 2H), 6.90 (d, 2H), 4.35–4.10 (m, 4H), 3.85 (s, 3H), 3.75 (s, 3H), 3.75–3.55 (m, 2H), 3.20–2.80 (m, 2 H), 1.90–1.40 (m, 4H)

(l) N-Methylsulfonyl-(D)-(4-methoxy)phenylalanylproline 2-methoxy-4-amidinobenzylamide acetate 0.23 g (2 mmol) of methanesulfonyl chloride was added to a solution of 0.9 g (2 mmol) of the above amidino [sic] hydrochloride in 20 ml of pyridine at 0° C., and the mixture was left to stir at room temperature overnight. The residue after removal of the solvent by distillation was purified by column chromatography (eluent: CH$_2$Cl$_2$)methanol/50% strength acetic acid, 45/5/1.5/. The eluate of pure fractions was distilled, adding toluene towards the end, and the residue was freeze dried. 0.5 g of acetate was obtained as white amorphous powder. FAB-MS: 531 (M$^+$).

EXAMPLE 2

N-Methylsulfonyl-(D)-phenylalanylproline (α-methyl-4-amidino)benzylamide (a) Benzophenone N-(p-cyanobenzyl) imine 270 g (2.0 mol) of anhydrous K$_2$CO$_3$ were added to a solution of 150 g (0.8 mol) of 97% pure benzophenone imine and 144.8 g (0.74 mol) of p-cyanobenzyl bromide in 450 ml of acetonitrile, and the mixture was left to stir at room temperature for 6 h. The inorganic salts were filtered off with suction and then most of the solvent was removed by distillation, 300 ml of water were added to the residue, and the mixture was extracted several times with ethyl acetate. The organic phase was washed 2× with water, dried over Na$_2$SO$_4$ and evaporated to dryness. Digestion with ether resulted in 180 g of white crystals, melting point 101–102° C.

(b) 1-(4-Cyanophenyl)ethylamine 20.7 g (0.07 mol) of benzophenone N-(p-cyanobenzyl) imine were added dropwise to a solution of lithium diisopropylamide, prepared from 8.15 g (0.08 mol) of diisopropylamine and 48.3 ml (0.08 mol) of a 15% strength solution of butyllithium in hexane, in 100 ml of abs. tetrahydrofuran at −70° C., and the mixture was left to stir for 15 minutes. Then 9.94 g (0.07 mol) of methyl iodide were added dropwise, and the temperature of the reaction mixture was allowed to rise to room temperature. After addition of 100 ml of water and several extractions with ether, the ether phase was washed with 5% strength citric acid solution, 5% strength NaHCO$_3$ solution and water and was dried over Na$_2$SO$_4$, and the ether was distilled off. The residue was dissolved in 150 ml of tetrahydrofuran, 100 ml of 1 N HCl were added, and the mixture was stirred at room temperature overnight. The tetrahydrofuran was distilled out of the reaction mixture under reduced pressure, the remaining acid phase was extracted several times with ether to remove the benzophenone, and then the acid phase was made alkaline with aqueous K$_2$CO$_3$ solution while cooling in ice, and the oily base was extracted with methylene chloride. The extract was dried over K$_2$CO$_3$. 9.7 g (95%) of a yellowish oil remained after stripping-off the methylene chloride and were used without further purification in the next reaction.

(c) Boc-(D)-phenylalanylproline (α-methyl-4-cyano) benzylamide 16.2 g of diisopropylamine and 22 ml (30 mmol) of propanephosphonic anhydride (50% strength solution in ethyl acetate) were added dropwise to a solution of 3.65 g (25 mmol) of 1-(4-cyanophenyl)ethylamine and 9.1 g (25 mmol) of Boc-D-Phe-Pro-OH in 150 ml of methylene chloride at −5° C. The mixture was then stirred for 2 h, during which the temperature was allowed to rise from −5° to 20° C. The organic phase was washed with water, 5%. strength sodium bicarbonate solution and 5% strength citric acid solution, dried over Na$_2$SO$_4$ and evaporated to dryness. A pale yellowish crystalline residue was obtained and was used without further purification in the next reaction.

(D)-Phenylalanylproline (α-methyl-4-amidino)benzylamide dihydrochloride 4.1 g of the above compound and 4 ml of triethylamine were dissolved in 40 ml of pyridine, saturated with H$_2$S at 0° C., and left to stand at room temperature overnight. A TLC check (CH$_2$Cl$_2$/MeOH, 9/1) showed that conversion to thioamide was complete. For isolation, most of the pyridine was removed by distillation under reduced pressure, and the residue was taken up in 250 ml of ethyl acetate and washed with brine, 5% strength citric acid solution and NaHCO$_3$ solution. Drying and removal of the solvent by distillation afforded 4.1 g of pure crystalline thioamide.

The thioamide was dissolved in 150 ml of acetone and, after addition of 7 ml of methyl iodide, left to stand at room temperature for 6 h. The amorphous residue after stripping off the solvent was extracted by stirring with dry ether and then dried. The methyl S-thioimidate hydroiodide was dissolved in 50 ml of ethanol, 15 ml of 10% strength ammonium acetate solution were added, and the mixture was heated at 60° C. for 3 h. For isolation, the solvent was stripped off, the residue was dissolved in 100 ml of CH$_2$Cl$_2$, the insolubles were filtered off and then the CH$_2$Cl$_2$ was distilled off. Digestion with an ethyl acetate/diethyl ether mixture removed the impurities soluble therein. The remaining iodide/acetate mixed salt was dissolved in acetone/water (3/2) and converted into the pure acetate using an IRA acetate ion exchange [sic], followed by freeze-drying. A white powder was isolated, melting point 110–115° C.

The above compound was dissolved in 70 ml of CH$_2$Cl$_2$, and 80 ml of HCl-saturated ethyl acetate were added. After a short time a precipitate separated out and was completed by adding ether. The latter was filtered off with suction, washed with ether until free of HCl [sic] and dried under reduced pressure. White crystals were obtained, melting point 190–195° C., FAB-MS: 407 (M$^+$).

(e) N-Methylsulfonyl-(D)-phenylalanylproline (α-methyl-4-amidino)benzylamide acetate The title compound was obtained as white amorphous powder as for 1e. FAB-MS: 485 (M$^+$).

EXAMPLE 3

N-Methylsulfonyl-(D)-cyclohexylalanylproline (2-methoxy-4-amidino)benzylamide 1.70 g (6.26 mmol) of Boc-(D)-Cha-OH were condensed as in Example 1j with 1.85 g (6.26 mmol) of proline (2-methoxy-4-cyano)benzylamide hydrochloride (Example 1i) to give 2.7 g of Boc-(D)-Cha-Pro (2-MeO-4-CN) benzylamide, and subsequently the Boc protective group was eliminated with HCl gas in DCM. 2.0 g (4.45 mmol) of H-(D)-Cha-Pro (2-MeO-4-CN)benzylamide hydrochloride were reacted in 40 ml of DCM and 8.9 mmol of diisopropylethylamine at 0° C. with 0.7 ml of methylsulfonyl chloride to give 2.0 g of the corresponding sulfonamide. The nitrile was converted by a known process (DE 41 21 947) via the thioamide stage into the amidine. Exchange of the amidine hydroiodide for the amidine hydroacetate (see Example 4b) resulted in 0.8 g of Me-SO$_2$-(D)-Cha-Pro (2-methoxy-4-amidino)benzylamide, which was purified by column chromatography as in Example 11. FAB-MS: (M+H)$^+$=496

EXAMPLE 4

N-Methylsulfonyl-(D,L)-diphenylalanylproline (2-methoxy-4-amidino)benzylamide (a) Boc-(D,L)-Dpa-Pro (2-MeO-4-CN)benzylamide 6.0 g (17.6 mmol) of Boc-(D,L)-Dpa-OH and 5.2 g (17.6 mmol) of H-Pro (2-MeO-4-CN)-benzylamide hydrochloride were reacted as in Example 1j and subsequently purified by column chromatography on silica gel (mobile phase: DCM/ 4.5% MeOH). 5.6 g of product were obtained.

$^1$H-NMR (DMSO-d$^6$; δ in ppm): 8.45 and 7.95 (1H, NH, (2 diastereomers or rotamers)), 7.5–6.9 (14H), 5.35–4.95 (m,1H), 4.5–4.1 (3H), 4.0–3.0 (3H), 3.90 and 3.85 (s,3H) (2 diastereomers)), 2.1–1.1 (13H)

(b) Me-SO$_2$-(D,L)-Dpa-Pro (2-MeO-4-amidino) benzylamide 3.55 g (6.0 mmol) of the Boc-protected compound (Example 4a) were cleaved in 30 ml of DCM with HCl gas to give 3.1 g of H-(D,L)-Dpa-Pro (2-MeO-4-CN) benzylamide hydrochloride, and 1.5 g (2.9 mmol) of this hydrochloride were stirred in 30 ml of DCM and 1.1 ml of diisopropylethylamine with 0.24 ml of methylsulfonyl chloride at 0° C. for 2 h. The organic phase was washed with 0.5 N HCl, water and saturated NaCl solution and then dried, and the product was purified by column chromatography on silica gel (mobile phase: DCM/5% MeOH). This resulted in 1.15 g of Me-SO$_2$-(D,L)-Dpa-Pro (2-MeO-4-CN) benzylamide. 1.15 g (2.1 mmol) of this nitrile were converted by a known process (DE 41 21 947) via the thioamide stage into the amidine. There were obtained 1.3 g of the thioamide and 0.95 g of the amidine hydroiodide, which was converted into the amidine hydroacetate on an ion exchanger (IRA 420). 0.77 g of Me-SO$_2$-(D,L)-Dpa-Pro (2-MeO-4-amidino)benzylamide hydroacetate (HPLC purity 95%) was obtained; FAB-MS: (M+H)$^+$=578

EXAMPLE 5

N-Methylsulfonyl-(D)-phenylalanylproline (6-amidino)-3-picolylamide acetate (a) 2-Cyano-5-(azidomethyl)pyridine 14.5 g (0.07 mol) of trifluoroacetic anhydride dissolved in 20 ml of methylene chloride were added dropwise to a solution of 8.8 g (0.07 mmol) of 2-cyano-5-(hydroxymethyl) pyridine (WO 83/01446) and 6.9 g of triethylamine in 200 ml of methylene chloride at room temperature, and the mixture was then stirred for 2 h. After removal of the methylene chloride by distillation, the residue was dissolved in a mixture of 50 ml of toluene and 50 ml of dimethyl sulfoxide, 11.2 g (0.17 mol) of sodium azide and 0.7 g of tetrabutylammonium bromide were added, and the mixture was stirred at room temperature overnight.

The reaction mixture was poured into 300 ml of water and extracted several times with ether. After drying with $Na_2SO_4$ and removal of the ether by distillation, 6.8 g of yellowish crystals remained and were used in the next reaction without further purification.

b) 2-Cyano-5-(aminomethyl)pyridine

The compound obtained in a) was dissolved in 45 ml of tetrahydrofuran and 1.2 ml of water and, while stirring, 11.2 g of triphenylphosphine were added in portions. The reaction mixture was left to stand at room temperature overnight. After removal of the solvent by distillation, the residue was taken up in 100 ml of ether, the precipitated triphenylphosphine oxide was filtered off with suction, and the filtrate was adjusted to pH 2 with ethereal hydrochloric acid. The precipitated hydrochloride was filtered off with suction, washed with ether and digested successively with toluene and hot isopropanol. 4.7 g (40%) of hydrochloride were isolated, melting point 253–256° C. (decomposition).

c) Boc-(D)-phenylalanylproline (6-cyano)-3-picolylamide 8.12 g of diisopropylethylamine, and subsequently 11 ml (15 mmol) of propanephosphonic anhydride (50% strength solution in ethyl acetate), were added dropwise to a solution of 2.11 g (12.5 mmol) of 2-cyano-5-(aminomethyl)pyridine and 4.5 g (12.5 mmol) of Boc-D-Phe-Pro-OH in 70 ml of $CH_2Cl_2$ at –5° C. The mixture was then stirred for 2 h, allowing the temperature to rise from –5° to 20° C. The organic phase was washed with water, 5% strength sodium bicarbonate and 5% strength citric acid solutions, dried over $Na_2SO_4$ and evaporated to dryness, a pale yellowish crystalline residue was obtained, melting point 167–170° C., which was used in the next reaction without further purification.

(d) N-Methylsulfonyl-(D)-phenylalanylproline (6-amidino)-3-picolylamide acetate

The above compound was dissolved in 100 ml of isopropanol and, after addition of a solution of 2.3 g of HCl in 20 ml of isopropanol, heated at 50° C. for 5 h, during which the hydrochloride of the deprotected compound separated out. This was filtered off with suction and washed with cold isopropanol until free of HCl.

2.5 g (6.5 mmol) of the above hydrochloride were suspended in 50 ml of $CH_2Cl_2$. Addition of 1.35 g (13.5 mmol) of triethylamine resulted in a solution to which, at 0 to 5° C., 0.7 g (6.1 mmol) of methanesulfonyl chloride dissolved in 10 ml of $CH_2Cl_2$ were added dropwise. The reaction mixture was stirred at room temperature for 5 h and then extracted by shaking with water, 5% strength citric acid and 5% strength $NaHCO_3$ solutions. After drying over $Na_2SO_4$ and removal of the solvent by distillation, the viscous oily residue was recrystallized from an ethyl acetate/ether mixture (1:1).

4.1 g of the above compound and 4 ml of triethylamine were dissolved in 40 ml of pyridine, saturated with $H_2S$ at 0° C., and left to stand at room temperature overnight. A TLC check ($CH_2Cl_2$/MeOH, 9/1) showed that conversion to thioamide was complete. For isolation, most of the pyridine was removed by distillation under reduced pressure, and the residue was taken up in 250 ml of ethyl acetate and washed with brine, 5% strength citric acid solution and $NaHCO_3$ solution. Drying and removal of the solvent by distillation afforded 4.1 g of pure crystalline thioamide.

The thioamide was dissolved in 150 ml of acetone and, after addition of 7 ml of methyl iodide, was left to stand at room temperature for 6 h. The amorphous residue after stripping off the solvent was extracted by stirring with dry ether and then dried. The methyl S-methylthioimidate hydroiodide was dissolved in 50 ml of ethanol, 15 ml of 10% strength ammonium acetate solution were added, and the mixture was heated at 60° C. for 3 h. For isolation, the solvent was stripped off, the residue was dissolved in 100 ml of $CH_2Cl_2$, the insolubles were filtered off and then the $CH_2Cl_2$ was distilled off. Digestion with an ethyl acetate/ diethyl ether mixture removed the impurities soluble therein. The remaining iodide/acetate mixed salt was dissolved in acetone/water (3/2) and converted into the pure acetate using an IRA acetate ion exchanger, followed by freeze-drying. A white amorphous powder was isolated, melting point 128–137° C., FAB-MS: 473 (M+H$^+$).

EXAMPLE 6

N-Methylsulfonyl-(D)-cyclohexylglycylproline (6-amidino)-3-picolylamide acetate (a) Boc-(D)-cyclohexylglycylproline 29 g (0.113 mol) of Boc-(D)-cyclohexylglycine and 18.7 g (0.113 mol) of proline methyl ester hydrochloride were suspended in 300 ml of $CH_2Cl_2$ and dissolved by dropwise addition of 58.3 g (0.45 mol) of diisopropylethylamine. After cooling to –15° C., 113 ml (0.147 mol) of propanephosphonic anhydride (50% strength solution in ethyl acetate) were added dropwise, and the mixture was stirred for 1 h.

After addition of 200 ml of water, the organic phase was separated off and washed with aqueous $K_2CO_3$ solution, 0.5 N hydrochloric acid and 5% strength bicarbonate solution. After drying with $Na_2SO_4$, the solvent was distilled off, the oily residue (41 g) was dissolved in 400 ml of ethanol, 120 ml of 1 N NaOH were added, and the mixture was stirred at room temperature for 2 h.

After removal of the alcohol by distillation, the aqueous phase was diluted with water and extracted several times with methyl tert-butyl ether. The aqueous phase was acidified with $KHSO_4$ solution and extracted 3× with $CH_2CL_2$. After drying and distilling off the methylene chloride, the oily residue was crystallized from diisopropyl ether/n-hexane (1/3). 28 g of white crystals were isolated, melting point 145–148° C.

b) Boc-(D)-cyclohexylglycylproline (6-cyano)-3-picolylamide 26.6 g (0.075 mol) of Boc-(D)-cyclohexylglycylproline and 12.7 g (0.075 mol) of 6-cyano-3-picolylamine hydrochloride were suspended in 300 ml of $CH_2Cl_2$, and 47 g (0.364 mol) of diisopropylethylamine were added. Then, at –10° C., 66 ml of propanephosphonic anhydride (50% strength ethyl acetate solution) were added dropwise, the mixture was stirred at 0° C. for 1 h, 200 ml of water were added, and the $CH_2Cl_2$ phase was separated off. The organic phase was washed with 0.1 N sodium hydroxide solution and water and then dried, and the solvent was distilled off. The residue was taken up in 100 ml of ethyl acetate, whereupon crystallization rapidly started and was completed by adding 150 ml of n-hexane. After filtration with suction and drying, 31.4 g (89% of theory) of white crystals, melting point 150–151° C., were isolated.

(c) N-Methylsulfonyl-(D)-cyclohexylglycylproline (6-amidino)-3-picolylamide acetate The protective group was eliminated from the above Boc compound as in Example 5d, reaction was carried out with methanesulfonyl chloride, and the cyano group was converted into the amidine. The acetate was isolated in the form of white crystals, melting point 250–256° C. (decomposition), FAB-MS: 465 (M+H$^+$).

EXAMPLE 7

N-Methylsulfonyl-(D)-cyclohexylglycylproline (5-amidino)-2-picolylamide acetate (a) 5-Carboxamido-2-picolylamine 3 g of Raney Ni were added to a solution of 3.5 g (24 mmol) of 2-cyano-5-carboxamidopyridine in 80 ml of methanol and 20 ml of concentrated ammonia, and hydrogenation was carried out at room temperature. Uptake of hydrogen was complete after about 7 h.

The filtrate after the catalyst had been filtered off with suction was concentrated and the residue was dissolved in 20 ml of 2 N hydrochloric acid and 20 ml of methanol. Addition of 150 ml of ethyl acetate resulted in separation out of the hydrochloride, which was filtered off with suction and dried (3.7 g). The free base melted at 198–202° C.

(b) 5-Cyano-2-picolylamine 41 g (0.22 mol) of 5-carboxamido-2-picolylamine were suspended in 150 ml of methanol and 300 ml of methylene chloride, cooled to 10° C., and dissolved by adding 150 ml of triethylamine. Then a solution of 47.6 g (0.22 mol) of (Boc)$_2$O was added dropwise, and the mixture was stirred at room temperature for 4 h.

The residue after the solvent had been stripped off was mixed with a saturated K$_2$CO$_3$ solution and extracted 5× with methylene chloride. The combined extracts were dried, and the solvent was distilled off, adding toluene toward the end. 5.4 g of the residue were suspended in 40 ml of dioxane and 15 ml of methylene chloride, 4.3 g of pyridine were added, and then, at 0° C., 5.2 g of trifluoroacetic anhydride were added dropwise, resulting in a clear solution.

Addition of 100 ml of water was followed by extraction with ethyl acetate, and the organic phase was washed with dilute citric acid, NaHCO$_3$ solution and water. A yellow oil (about 5 g) remained after drying and stripping off the solvent, and was dissolved in 15 ml of isopropanol and 30 ml of ethyl acetate, and 35 ml of etherial hydrochloric acid solution were added. After standing overnight, the precipitated hydrochloride was filtered off with suction and dried. 4 g of white crystals were isolated. Melting point 230–234° C.

(c) Boc-(D)-cyclohexylglycylproline (5-cyano)-2-picolylamide

Boc-(D)-cyclohexylglycine-proline [sic] was coupled with 5-cyano-2-picolylamine as in Example 6b to result in white crystals, melting point 128–129° C.

(d) N-Methylsulfonyl-(D)-cyclohexylglycylproline (5-amidino)-2-picolylamide acetate The protective group was eliminated from the above Boc compound as in Example 5d, reaction was carried out with methanesulfonyl chloride, and the cyano group was converted into the amidine. The acetate was isolated in the form of white crystals, melting point 149–150° C. (decomposition),

FAB-MS: 465 (M+H$^+$).

EXAMPLE 8

N-Methylsulfonyl-(D)-cyclohexylalanyl-3,4-dehydroproline (6-amidino)-3-picolylamide acetate (a) Boc-3,4-dehydroproline (6-carboxamido)-3-picolylamide 5.0 g of Boc-3,4-dehydroproline (23.4 mmol) were suspended together with 5.25 g of 6-carboxamido-3-picolylamine dihydrochloride and 32.1 ml of diisopropylethylamine (187 mmol) in 50 ml of CH$_2$Cl$_2$ and, while stirring at 0 to 5° C., 23.5 ml of propanephosphonic anhydride (50% strength solution in ethyl acetate) were added dropwise. The mixture was then stirred at room temperature overnight. The solution was diluted to 150 ml with CH$_2$Cl$_2$, extracted successively with 20% strength sodium bisulfate solution and 5% strength citric acid solution, dried over sodium sulfate and concentrated in a rotary evaporator. The aqueous phases were back-extracted three times with CH$_2$Cl$_2$, and the organic phase was dried, concentrated in a rotary evaporator and employed together with the main product without further purification in the next reaction.

(b) H-3,4-dehydroproline (6-carboxamido)-3-picolylamide hydrochloride

The crude product from a) was dissolved in 100 ml of CH$_2$Cl$_2$ and, after addition of 10 ml of 5M HCl in ether, stirred at room temperature for 2 h (TLC check). The crude product after complete evaporation to dryness under reduced pressure and codistillation with toluene under reduced pressure was recrystallized from 200 ml of ethanol. This resulted in 5.03 g and, after concentration of the mother liquor, a further 0.3 g of product. (80.4% of theory). Elemental analysis showed that the product was in the form of the monohydrochloride.

(c) Boc-(D)-cyclohexylalanyl-3,4-dehydroproline (6-carboxamido)-3-picolylamide 5.06 g of Boc-(D)-cyclohexylalanine (18.66 mmol) were stirred together with 5.28 g of H-3,4-dehydroproline (6-carboxamido)-3-picolylamide hydrochloride (18.66 mmol) and 9.55 ml of diisopropylethylamine (56 mmol) in 75 ml of CH$_2$Cl$_2$ and, at 0 to 5° C., 18.6 ml of propanephosphonic anhydride (50% strength solution in ethyl acetate) were added dropwise. The mixture was then stirred at room temperature overnight, during which a precipitate separated out. After the precipitate had been filtered off with suction and the solution had been extracted five times with 25 ml of 5% strength citric acid each time (TLC showed no diisopropylethylamine left in the organic phase), the organic phase was washed several times with saturated sodium bicarbonate solution, dried over sodium sulfate and concentrated under reduced pressure. To minimize the propanephosphonic acid byproduct, the residue was taken up in ethyl acetate, extracted several times with saturated bicarbonate solution and then dried over sodium sulphate and concentrated in a rotary evaporator. Yield 7.0 g of product as solidified foam (75% of theory).

(d) Boc-(D)-cyclohexylalanyl-3,4-dehydroproline (6-cyano)-3-picolylamide 7.0 g of Boc-(D)-cyclohexylalanyl-3,4-dehydroproline (6-carboxamido)-3-picolylamide (14 mmol) were dissolved together with 9.5 ml of diisopropylethylamine (56 mmol) in 100 ml of methylene chloride, cooled to 0 to 5° C., and 3.5 ml of trifluoroacetic anhydride (25.2 mmol) were added dropwise. After stirring at room temperature for 2 h, the precursor was completely converted (TLC check). The solution was then extracted three times with 25% strength sodium sulfate solution, three times with saturated sodium bicarbonate solution and once with saturated brine, dried over sodium sulfate and concentrated in a rotary evaporator. Yield: 6.6 g (98% of theory).

(e) Preparation of H-(D)-cyclohexylalanyl-3,4-dehydroproline (6-cyano)-3-picolylamide 6.6 g of Boc-(D)-cyclohexylalanyl-3,4-dehydroproline (6-cyano)-3-picolylamide (13.75 mmol) were dissolved in 15 ml of isopropanol and, after addition of 12.5 ml of 4N isopropanolic hydrochloric acid solution, stirred at 40° C. for 2 h (TLC check). The reaction solution was concentrated under reduced pressure, the residue was taken up in water, the solution was extracted three times with ether, and the aqueous phase was adjusted to pH 9 with 20% strength sodium hydroxide solution and extracted several times with CH$_2$Cl$_2$. The organic phase was washed with saturated brine, dried over sodium sulfate and concentrated in a rotary evaporator to result in 4.3 g of product (82% of theory).

(f) Preparation of methylsulfonyl-(D)-cyclohexylalanyl-3,4-dehydroproline (6-cyano)-3-picolylamide The compound was prepared as in Example 5d from H-(D)-cyclohexylalanyl-3,4-dehydroproline (6-cyano)-3-picolylamide and methanesulfonyl chloride. Yield: 95% of theory.

(g) Preparation of methylsulfonyl-(D)-cyclohexylalanyl-3,4-dehydroproline (6-amidino)-3-picolylamide This compound was prepared as in Example 5d from methylsulfonyl-(D)-cyclohexylalanyl-3,4-dehydroproline (6-cyano-3-picolyl)amide via the thioamide and methyl S-methylthioamidate hydroiodide. A white amorphous powder was isolated. FAB-MS (M+H)$^+$=477

EXAMPLE 9

N-Methylsulfonyl-(D)-cyclohexylglycyl-3,4-dehydroproline (6-amidino)-3-picolylamide acetate This compound was prepared as in Example 8. White amorphous powder, FAB-MS (M+H)$^+$=463.

EXAMPLE 10

N-(Hydroxycarbonylmethylene)sulfonyl-(D)-cyclohexylglycylproline (6-amidino)-3-picolylamide H-(D)-cyclohexylglycylproline (6-cyano)-3-picolylamide (Example 6b) was reacted with methoxycarbonylmethylenesulfonyl chloride (preparation disclosed in Tetrahedron Letters 30 (1989) 2869) to synthesize the corresponding sulfonamide. The nitrile functionality was converted into the amidine group via the thioamide stage by known processes (DE 41 21 947).

The resulting N-(methoxycarbonylmethylene)sulfonyl-(D)-cyclohexylglycylproline (6-cyano)-3-picolylamide product was heated in a mixture of 4N hydrochloric acid and dioxane at 80° C. to hydrolyze the ester functionality (TLC check), and then the solution was concentrated and the residue was purified by HPLC on an RP column, and the aqueous phases were lyophilized; amorphous powder FAB-MS (M+H)$^+$509.

We claim:

1. A thrombin inhibitor compound of the formula I

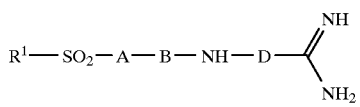

or a stereoisomer thereof or a salt thereof with a physiologically tolerated acid, where the amidine functionality can be in mono- or diprotected form and in which the substituents have the following meanings:

R$^1$ is OH, C$_1$–C$_{20}$-alkyl, C$_1$–C$_3$-fluoroalkyl, C$_3$–C$_8$-cycloalkyl, aryl-C$_1$–C$_{10}$-alkyl, aryl, hetaryl, R$^2$OOC—(CH$_2$)$_n$ or R$^3$R$^2$N, where R$^2$ and R$^3$ are identical or different and are hydrogen, C$_1$–C$_{10}$-alkyl, aryl, aryl-C$_1$–C$_{10}$-alkyl or together are a C$_2$–C$_7$-alkylene chain to which an aryl or hetaryl radical can be fused or which can contain a hetero atom (O, S, NH or substituted N), and n is 1, 2, 3 or 4, A: is an α-amino acid residue of the formula II

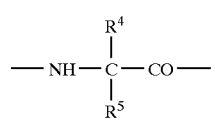

where

R$^4$ is hydrogen, C$_1$–C$_8$-alkyl, C$_3$–C$_7$-cycloalkyl, aryl or aryl-C$_1$–C$_3$-alkyl, R$^5$ is hydrogen, C$_1$–C$_8$-alkyl, C$_3$–C$_7$-cycloalkyl or C$_3$–C$_7$-cycloalkyl-CH$_2$—, it being possible for a CH$_2$ group to be replaced by O, S, NR$^6$, or bicycloalkyl-(CH$_2$)$_{0,1}$, adamantyl-(CH$_2$)$_{0-1}$, (CH$_3$)$_3$Si—C$_1$–C$_4$-alkyl, aryl or aryl-C$_1$–C$_3$-alkyl, hetaryl or hetaryl-C$_1$–C$_3$-alkyl, if R$^4$ is H, a C$_1$–C$_8$-alkyl radical in which a hydrogen atom is replaced by SR$^6$, OR$^6$, CO—OR$^6$ (R$^6$=hydrogen, C$_1$–C$_8$-alkyl or aryl-C$_1$–C$_3$-alkyl) or CONR$^7$R$^8$ (R$^7$, R$^8$ are identical or different and are H, C$_1$–C$_4$-alkyl, C$_3$–C$_7$-cycloalkyl or together are a C$_3$–C$_6$-alkylene chain), or R$^4$ and R$^5$ together are a C$_2$–C$_6$-alkylene chain which may contain a fused-on aryl radical, B: is a cyclic α-amino acid residue of the formula III

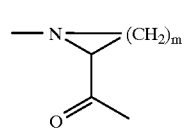

where m is 2, 3 or 4, and a hydrogen on the ring can be replaced by a hydroxyl or C$_1$–C$_3$-alkyl group and, if m is 3 or 4, a CH$_2$ group in the ring can be replaced by oxygen, sulfur, NH or N—C$_1$–C$_4$-alkyl and/or two vicinal hydrogen atoms can be replaced by a double bond or by a fused-on aromatic system or a methylene chain with 4–6 carbon atoms, D: is a structural fragment of the formula IV, V or VI

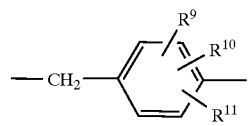

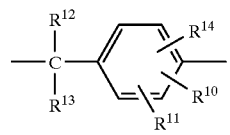

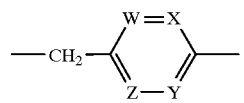

where
- $R^9$ is F, Cl, Br, $NO_2$, $R^{15}O$, $R^{15}OOC$, $R^{15}OCH_2$, $R^{15}NH-CO$, $R^{15}NH$, $R^{15}CONH$ or $R^{15}OOCCH_2O$, where $R^{15}$ is H, $C_1$–$C_6$-alkyl, benzyl or phenyl,
- $R^{10}$, $R^{11}$ are H, $C_1$–$C_4$-alkyl or $R^{15}O$, where $R^9$ and $R^{10}$ or $R^{11}$ may together form a fused-on phenylene ring or an alkylene chain consisting of 3 to 5 carbon atoms, in which one or two carbon atoms can be replaced by oxygen,
- $R^{12}$ is H or $C_1$–$C_4$-alkyl,
- $R^{13}$ is $C_1$–$C_4$-alkyl, phenyl-$C_1$–$C_4$-alkyl, $R^{15}CO$, $CF_3CO$, $C_2F_5CO$, $R^{15}OCH_2$, $R^{15}OOC$, $R^{15}OCH_2CO$, $R^{15}OOCCO$ or $R^{15}NHCOCO$,
- $R^{14}$ is H, $C_1$–$C_4$-alkyl, F, Cl, Br, $NO_2$, $R^{15}O$, $R^{15}OOC$, $R^{15}OCH_2$, $R^{15}CO$, $R^{15}CONH$, $R^{15}NH-CO$ or $R^{15}OOCCH_2O$, and W, X, Y, Z are CH or N, but at least one of the radicals W, X, Y or Z is N and the ring in VI can be substitued by 1 or 2 of the following radicals: $C_1$–$C_4$-alkyl, OH, O—$C_1$–$C_4$-alkyl, $CF_3$, F, Cl, Br, S—$C_1$–$C_4$-alkyl, $O(CH_2)_n COOR^6$ (n=1–4).

2. A compound of the formula VII, VIII, IX or X, according to claim 1,

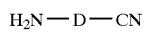

VII

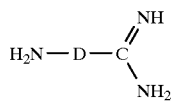

VIII

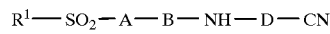

IX

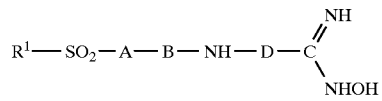

X where $R^1$, A, B, D, W, X, Y and Z have the meanings stated in claim 1, and where the amidine functionality in formula VIII can be in mono- or diprotected form.

3. The thrombin inhibitory compound defined in claim 1, which comprises a structural fragment XI,

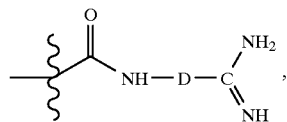

XI where D is a structural fragment of the formula IV, V or VI

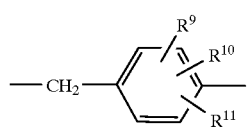

IV

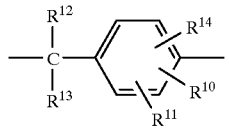

V

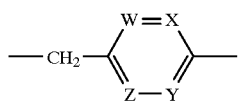

VI where
- $R^9$ is F, Cl, Br, $NO_2$, $R^{15}O$, $R^{15}OOC$, $R^{15}OCH_2$, $R^{15}NH-CO$, $R^{15}NH$, $R^{15}CONH$ or $R^{15}OOCCH_2O$, where $R^{15}$ is H, $C_1$–$C_6$-alkyl, benzyl or phenyl,
- $R^{10}$, $R^{11}$ are H, $C_1$–$C_4$-alkyl or $R^{15}O$, where $R^9$ and $R^{10}$ or $R^{11}$ may together form a fused-on phenylene ring or an alkylene chain consisting of 3 to 5 carbon atoms, in which one or two carbon atoms can be replaced by oxygen,
- $R^{12}$ is H or $C_1$–$C_4$-alkyl,
- $R^{13}$ is $C_1$–$C_4$-alkyl, phenyl-$C_1$–$C_4$-alkyl, $R^{15}CO$, $CF_3CO$, $C_2F_5CO$, $R^{15}OCH_2$, $R^{15}OOC$, $R^{15}OCH_2CO$, $R^{15}OOCCO$ or $R^{15}NHCOCO$,
- $R^{14}$ is H, $C_1$–$C_4$-alkyl, F, Cl, Br, $NO_2$, $R^{15}O$, $R^{15}OOC$, $R^{15}OCH_2$, $R^{15}CO$, $R^{15}CONH$, $R^{15}NH-CO$, $R^{15}OOCCH_2O$ and W, X, Y, Z are CH or N, but at least one of the radicals W, X, Y or Z is N and the ring in VI can be substituted by 1 or 2 of the following radicals: $C_1$–$C_4$-alkyl, OH, O—$C_1$–$C_4$-alkyl, $CF_3$, F, Cl, Br, S—$C_1$–$C_4$-alkyl, $O(CH_2)_n COOR^6$ (n=1–4).

4. A method of preventing thrombin-dependent early reocclusion and later restenosis after percutaneous transluminal coronary angioplasty, thrombin-induced proliferation of smooth muscle cells, accumulation of active thrombin in the CNS, and mechanisms leading to adhesion and metastasis of cancer cells, which method comprises administering to a patient an effective amount of a compound of formula I as defined in claim 1.

5. A method of treating deep vein thrombosis, pulmonary embolism, myocardial or cerebral infarct, unstable angina and disseminated intravascular coagulation, which method comprises administering to a patient an effective amount of the compound of formula I as defined in claim 1.

* * * * *